| United States Patent [19] | [11] Patent Number: 5,055,304 |
| Makino et al. | [45] Date of Patent: Oct. 8, 1991 |

[54] STABILIZED PHARMACEUTICAL COMPOSITION AND METHOD OF PRODUCING SAME

[75] Inventors: Tadashi Makino, Ibaraki; Koji Doi, Suita, both of Japan

[73] Assignee: Senju Pharmaceutical Co., Ltd., Osaka, Japan

[21] Appl. No.: 360,867

[22] Filed: Jun. 2, 1989

[30] Foreign Application Priority Data

Jun. 3, 1988 [JP] Japan .................................. 63-137924

[51] Int. Cl.$^5$ .......................... A61K 9/20; A61K 9/50; A61K 31/70
[52] U.S. Cl. .................................... 424/465; 424/502; 514/47; 514/970
[58] Field of Search .................. 514/47, 970; 424/465, 424/502

[56] References Cited

FOREIGN PATENT DOCUMENTS 50-88218  7/1975  Japan .
50-128420 9/1976 Japan .

OTHER PUBLICATIONS

See the enclosed abstract for France Patent #1975.
Chemical Abstracts, vol. 97 (133597z), 1982.

Primary Examiner—Frederick E. Waddell
Assistant Examiner—Kevin Weddington
Attorney, Agent, or Firm—Wenderoth, Lind & Ponack

[57] ABSTRACT

The present invention provides stable pharmaceutical compositions containing disodium adenosine triphosphate (ATP-2Na) which are advantageous in that, as a result of the addition of a low-melting fat- or oil-like substance to ATP-2Na, the decomposition or the like of ATP-2Na is prevented and the content of ATP-2Na can be maintained at a high level even after the lapse of a number of days.

The compositions according to this invention can be used advantageously, for example, in the treatment of cerebrovascular disorder, cardiac failure and asthenopia.

7 Claims, No Drawings

STABILIZED PHARMACEUTICAL COMPOSITION AND METHOD OF PRODUCING SAME

BACKGROUND OF THE INVENTION

1. Field of the Invention

This invention relates to a stabilized pharmaceutical composition prepared by admixing a low-melting fat- or oil-like substance with disodium adenosine triphosphate (hereinafter sometimes referred to briefly as "ATP-2Na"), which is useful, for example, in alleviating or treating cerebrovascular disorder, cardiac failure and asthenopia, and to a method of producing such composition.

2. Description of the Prior Art

Since the discovery by Fiske and Lohmann et al. (1929) of adenosine triphosphate (hereinafter sometimes referred to briefly as "ATP") occurring in muscular tissue infusions, the role of disodium adenosine triphosphate in living organisms has been elucidated step by step by a number of researchers. As a representative of the compounds having the so-called energy rich phosphate bond, ATP is found everywhere in living organisms. The energy required in living organisms is supplied solely by ATP. On the other hand, the clinical use of ATP-2Na as a therapeutic agent has become fairly popular and its efficacy has been established in certain diseases.

While ATP-2Na is useful as a therapeutic agent for various purposes, as mentioned above, it has drawbacks. Thus, in the solid form, it is unstable under high temperature and/or high humidity conditions and, in the form of an aqueous solution or suspension, its stability decreases with the decreasing pH value. Therefore, preparations or dosage forms containing it, particularly tablets, have poor stability as far as ATP-2Na is concerned. The content of the active ingredient in said preparations decreases with the lapse of time and coloration occurs before long.

In some pharmaceutical compositions containing other ingredients, ATP-2Na strongly interacts with said other ingredients, leading to still more decreased stability. Furthermore, in the case of tablets, crystals are distorted due to the pressure, friction, heat and other effects applied or produced in the step of molding under pressure and as a result, the fall in content with the lapse of time is accelerated in many instances.

While, as mentioned above, ATP-2Na is under research and development for use as an agent for treating or alleviating various diseases, the stability problem in producing preparations containing it has not been solved to a satisfactory extent as yet. In particular, the art has not yet known any technology that could prevent such decomposition of the active ingredient ATP-2Na with the lapse of time as mentioned above and thereby improve the stability of ATP-2Na preparations produced in the form of solid preparations such as tablets and therefore could be put to practical use. As a result, the conventional ATP-2Na preparations are disadvantageous without exception particularly in that their quality can be guaranteed only for a short period of time and that they must be stored in a cool place.

Accordingly, it is an object of the invention to provide a stabilized ATP-2Na preparation. Another object is to provide a means of stabilizing ATP-2Na which is quite practicable from the cost viewpoint as well and which is other than those prior art means that often lead to increases in drug preparation cost. such as extra charge of drugs, extreme reduction of water content, etc. A further object of the invention is to provide such means of stabilizing ATP-2Na preparations to thereby prolong the period over which the quality of products can be guaranteed. make the products storable under less strict conditions and heighten the commercial value of the products.

Under the circumstances such as mentioned above, the present inventors made various attempts to stabilize ATP-2Na-containing preparations by addition of bases. clathration with cyclodextrins and the like, and addition of antioxidants, among others, but failed to find out any stabilizing effect of satisfactorily practical significance. As a result of further investigations, however, the present inventors unexpectedly found that when a low-melting fat- or oil-like substance is incorporated into ATP-2Na preparations, the decomposition of ATP-2Na can be prevented to a remarkable extent and stable preparations can be obtained. As a result of continued investigations based on this finding, they have now completed the present invention.

SUMMARY OF THE INVENTION

Thus, the present invention is directed to: (1) a stabilized pharmaceutical composition which contains disodium adenosine triphosphate and a low-melting fat- or oil-like substance; and (2) a method of producing a stabilized pharmaceutical composition which comprises admixing a low-melting fat- or oil-like substance with disodium adenosine triphosphate and molding the resulting mixture under pressure.

DETAILED DESCRIPTION OF THE INVENTION

ATP-2Na, which is to be used in the practice of the invention, has the following structure:

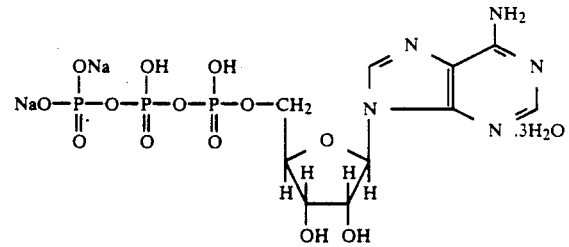

The main reaction involved in the decomposition of this substance is said to be hydrolysis. Thus, the decomposition proceeds from ATP-2Na to ADP (disodium adenosine diphosphate) and then to AMP (disodium adenosine monophosphate). Further decomposition is accompanied by the phenomenon of browning.

The low-melting fat- or oil-like substance to be used in accordance with the invention may be any of fatty, oily or waxy substances with a relatively low melting point and without producing any unfavorable effect on ATP-2Na, such as, for example, hydrocarbons, higher fatty acids, higher alcohols, polyhydric alcohol fatty acid esters, polyhydric alcohol higher alcohol ethers and alkylene oxide polymers or copolymers. Preferred among these are polyhydric alcohol fatty acid esters, polyhydric alcohol higher alcohol ethers and alkylene oxide polymers or copolymers.

As the hydrocarbons, there may be mentioned, among others, n-alkanes containing 17 to 50 carbon atoms, such as n-heptadecane, n-octadecane, n-nonadecane, n-eicosane, n-heneicosane, n-docosane, n-tricosane, n-tetracosane, n-pentacosane, n-triacontane, n-pentatriacontane, n-tetracontane and n-pentacontane, and mixtures of these (petrolatum, paraffin wax, microcrystalline wax, etc.).

As the higher fatty acids, there may be mentioned, for example, capric acid, lauric acid, myristic acid, palmitic acid, stearic acid, arachidic acid, behenic acid, lignoceric acid, cerotic acid, mixtures of these, and other higher fatty acids derivable from naturally occurring fats and oils.

As the higher alcohols, there may be mentioned lauryl alcohol, myristyl alcohol, cetyl alcohol, stearyl alcohol, arachyl alcohol, mixtures of these, other higher alcohols derivable from naturally occurring oils, and so forth.

As the polyhydric alcohol fatty acid esters, there may be mentioned, for instance, esters derived from an alcohol having two or more hydroxyl groups within the molecule (e.g. alkylene glycol such as ethylene glycol or propylene glycol, polyalkylene glycol such as polyethylene glycol, polypropylene glycol or copolymer of these, saccharide such as sorbitol, sucrose or raffinose, intramolecular dehydration product derived from sorbitol, such as 1,5-sorbitan, 1,4-sorbitol or 3,6-sorbitan, glycerin, diethanolamine, pentaerythritol) and a fatty acid (e.g. acetic acid, propionic acid, butyric acid, pelargonic acid, capric acid, undecylenic acid, lauric acid, tridecylic acid, myristic acid, pentadecylic acid, palmitic acid, heptadecylic acid, stearic acid, nonadecanoic acid, undecylenic acid, oleic acid, elaidic acid, sorbic acid, linoleic acid, linolenic acid, arachidonic acid, stearolic acid), more specifically, sorbitan fatty acid esters having a molecular weight of 400 to 900, such as sorbitan monostearate, sorbitan tristearate, sorbitan monooleate, sorbitan sesquioleate and sorbitan monopalmitate, polyoxyalkylenesorbitan fatty acid esters having a molecular weight of 1,000 to 1,500, such as polyoxyethylenesorbitan tristearate, polyoxyethylenesorbitan monooleate and polyoxyethylenesorbitan tripalmitate, polyoxyalkylenesorbitol fatty acid esters such as polyoxyethylenesorbitol hexastearate, polyoxyethylenesorbitol hexaoleate, polyoxyethylenesorbitol tristearate and polyoxyethylenesorbitol tetralaurate, polyoxyalkylenesorbitol beeswax derivatives such as polyoxyethylenesorbitol beeswax derivatives, polyoxyalkylenelanolin derivatives such as polyoxyethylenelanolin derivatives, propylene glycol fatty acid esters having a molecular weight of 200 to 700, such as propylene glycol monopalmitate, propylene glycol monostearate, propylene glycol dilaurate, propylene glycol dimyristate, propylene glycol dipalmitate and propylene glycol distearate, and ethylene glycol fatty acid esters having a molecular weight of 500 to 1,200, such as ethylene glycol monolaurate, ethylene glycol palmitate, ethylene glycol margarate, ethylene glycol stearate, ethylene glycol dilaurate, ethylene glycol dimyristate, ethylene glycol dipalmitate and ethylene glycol dimargarate, other alkylene glycol fatty acid esters, polyoxyalkylene-castor oil derivatives having a molecular weight of 3,500 to 4,000, such as polyoxyethylene-castor oil derivatives, polyoxyalkylene fatty acid esters having a molecular weight of 1,900 to 2,200, such as polyoxyethylene stearate, polyoxyethylene oleate, polyoxyethylene palmitate and polyoxyethylene linoleate, glycerin mono-fatty acid esters having a molecular weight of 300 to 600, such as glycerin monoacetate, glycerin monopropionate, glycerin monostearate, glycerin monooleate, glycerin monopalmitate and glycerin monolinoleate, sucrose fatty acid esters having a molecular weight of 400 to 1,300, such as sucrose monolaurate, sucrose monomyristate, sucrose monopalmitate, sucrose monostearate, sucrose trimysristate, sucrose tripalmitate and sucrose tristearate, and so forth.

As the polyhydric alcohol higher alcohol ethers, there may be mentioned ethers derived from a polyhydric alcohol (as mentioned above as the alcohol component of the polyhydric alcohol fatty acid esters) and higher fatty alcohol (e.g. cetyl alcohol, stearyl alcohol, oleyl alcohol, octyl alcohol, decyl alcohol). More specifically, those usable in many instances are, for example, polyoxyethylene higher alcohol ethers such as polyoxyethylene lauryl ether, polyoxyethylene cetyl ether, polyoxyethylene stearyl ether, polyoxyethylene oleyl ether, polyoxyethylene octyl ether and polyoxyethylene decyl ether, and polyoxypropylene-polyoxyethylene higher alcohol ethers such as polyoxypropylene-polyoxyethylene cetyl ether, polyoxypropylene-polyoxyethylene stearyl ether, polyoxypropylene-polyoxyethylene oleyl ether, polyoxypropylene-polyoxyethylene octyl ether and polyoxypropylene-polyoxyethylene lauryl ether.

As the alkylene oxide polymers, those having a molecular weight of 1,000 to 10,000 (e.g. polyethylene glycol 6000) may be used. As the alkylene oxide, there may be mentioned, among others, ethylene oxide, propylene oxide, trimethylene oxide and tetrahydrofuran.

As the alkylene oxide copolymers, copolymers of two or more of the alkylene oxides mentioned above and having a molecular weight of 1,000 to 10,000 may be used.

Of these low-melting fat- or oil-like substances those having a melting point of about 20° to 90° C. may generally be used. Ones having a melting point of 20° to 60° C. are particularly preferred. These low-melting fat- or oil-like substances may be used either singly or in the form of a mixture of two or more of them.

These low-melting fat- or oil-like substances are added, either in the solid form or in the liquid form, to ATP-2Na. When they are added in the solid form (as a powder), the low-melting fat- or oil-like substances are used in an amount of at least 0.1 part by weight, generally about 0.1 to 3 parts by weight, preferably about 0.2 to 1 part by weight, per part by weight of ATP-2Na. When they are added in the liquid form (as a solution), the low-melting fat- or oil-like substances are used in an amount of at least 0.1 part by weight, generally about 0.1 to 3 parts by weight, preferably 0.2 to 0.8 part by weight.

The present invention is more advantageously applicable to solid preparations or dosage forms containing ATP-2Na.

Generally, the solid preparations according to the invention are produced by admixing a low-melting fat- or oil-like substance such as mentioned above to ATP-2Na and then molding the resulting mixture under pressure. The admixing is effected by any means of admixing commonly used in producing pharmaceutical preparations, for example by blending, kneading, comalaxating, sieving or agitating. For instance, the low-melting fat- or oil-like substance may be added directly to ATP-2Na and the materials blended (addition in powder form) or a solvent may be added and the materials blended, kneaded, granulated and dried by conventional methods. Alternatively, it is also possible to dissolve the low-melting fat- or oil-like substance in an appropriate solvent, admix the solution with ATP-2Na uniformly and knead, granulate and dry, or treat otherwise, the resulting mixture by conventional methods (addition in solution form). Usable as said appropriate solvent for the addition in solution form are, for example, water, dimethylformamide, acetone, ethanol, propyl alcohol, isopropyl alcohol, butyl alcohol, methylene chloride, trichloroethane and other solvents which will not exert any unfavorable effect on ATP-2Na. After achieving uniform admixture, the resulting composition can be molded under pressure by a known method to give ATP-2Na-containing solid preparations. The term "molding under pressure" as used herein means compression under pressure to give a desired shape or form and, in most cases, said term means tableting, among others. Presumably, the incorporation of said low-melting fat- or oil-like substances results in decreased strain of crystals in the step of molding under pressure and, furthermore, in improved moldability, so that a lower pressure becomes sufficient for the molding purposes. In the process for producing the composition according to the invention, one or more of various additives known to be usable in solid-form preparations may be added to said composition in an appropriate step or steps. Thus, for example, excipients or carriers such as crystalline cellulose (e.g. Avicel PH101, Asahi Chemical Industry), celluloseglycolic acid calcium salt, corn starch, wheat starch, sucrose, glucose, calcium sulfate, calcium phosphate, sodium chloride, etc., binders such as gum arabic, gelatin, methylcellulose, polyvinylpyrrolidone, hydroxypropylcellulose (hereinafter sometimes referred to briefly as "HPC"), hydroxypropylmethylcellulose, etc., lubricants such as magnesium stearate, talc, synthetic aluminum silicate, sodium lauryl sulfate, boric acid, magnesium oxide, paraffin, etc., colorants, flavors, corrigents, and the like may be added.

Furthermore, since ATP-2Na is unstable to acids, it is desirable to subject the composition according to the invention to enteric coating to prevent the decomposition of ATP-2Na in gastric juice. The enteric coating can be performed by any per se known method. Usable coating materials for such purpose are those generally used as enteric coating materials, for example, cellulose acetate phthalate, hydroxypropylmethylcellulose phthalate, hydroxymethylcellulose acetate succinate, carboxymethylcellulose, methacrylic acid-acrylic acid copolymers [e.g. Eudragit L30D-55 (Rohm, West Germany)], shellac, polyethylene glycol, polysorbates (e.g. Tween 80), polyoxyethylene-polyoxypropylene glycol (e1g. Pluronic F68), castor oil, triacetin, talc, and colorants such as titanium oxide and red iron oxide.

The composition according to the invention may be sugar-coated. The sugar-coated tablets can be produced by any known coating technique using a conventional coating agent or composition. Usable as such coating composition are, for example, sugar coating compositions prepared by using granulated sugar, talc, pullulan, powdered gum arabic (acacia), crystalline cellulose, etc. Combination drug preparations may also be prepared from said composition and some other pharmaceutically active ingredient or ingredients. Such combination drug preparations may be produced, for example in the form of multiple compressed tablets, by dry-coating enteric-coated ATP-containing tablets with said other active ingredient or ingredients.

The ATP-2Na-containing solid preparations obtained in the above manner by admixing ATP-2Na with a low-melting fat- or oil-like substance are stable and show no changes in appearance (browning etc.), with the decomposition during storage as resulting from the molding under pressure being inhibited. In the treatment of cerebrovascular disorder, cardiac failure or asthenopia in mammals, the pharmaceutical composition according to the invention can be administered orally in the form of tablets, for instance, at a daily dose of about 0.7 to 7.0 mg/kg, preferably about 2 to 3 mg/kg, as ATP-2Na.

EXAMPLES

The following examples will illustrate the invention in further detail but are by no means limitative of the scope of the invention.

EXAMPLE 1

Polyethylene glycol 6000 was used as the low-melting fat- or oil-like substance and admixed with ATP-2Na and other ingredients according to the formulation shown below using a fluidized bed granulator (Fuji Sangyo model FD-3S) In said granulator, the resultant mixture was sprayed [with an aqueous solution of hydroxypropylcellulose (binder solution) and granulated, and dried. The granular composition thus obtained was sieved, then supplemented with magnesium stearate and tableted on a tableting machine (Kikusui Seisakusho model Correct 19K) using a 4.5 R punch (6.0 mm $\phi$) at a pressure of 1.0 ton/cm². The thus-obtained tablets each weighing 90 mg were stored at 60° C. or 40° C. for stability testing.

| Material | Formulation Invention A | Control B |
|---|---|---|
| ATP-2Na | 20.0 mg | 20.0 mg |
| Lactose | 49.5 | 55.5 |
| Corn starch | 10.0 | 10.0 |
| Polyethylene glycol 6000 | 6.0 | — |
| Hydroxypropylcellulose L | 2.5 | 2.5 |
| (Water) | (44.0 μl) | (44.0 μl) |
| Subtotal | 88.0 mg | 88.0 mg |
| Corn starch | 1.5 | 1.5 |
| Magnesium stearate | 0.5 | 0.5 |
| Total | 90.0 mg | 90.0 mg |

| Results of storage stability testing | | | | | |
|---|---|---|---|---|---|
| | | Control Stabilizing agent | | | |
| Invention | Control | Magnesium carbonate | Sodium hydrogen carbonate | Cysteine | β-Cyclodextrin |

| Item | A | B | (C) | (D) | (E) | (F) |
|---|---|---|---|---|---|---|
| At the start of testing (hereinafter, "initial") | (100) | (100) | (100) | (100) | (100) | (100) |
| After storage at 60° C. for 1 week | 98 | 78 | 52 | 50 | 80 | 76 |
| After storage at 40° C. for 4 weeks | 100 | 96 | — | — | — | — |

In the storage stability testing, the residual content of ATP-2Na after the lapse of each storage period was determined by liquid chromatography and expressed in terms of percent residue. Also tested as controls were a preparation (B) with no stabilizing agent added and preparations (C to F) with the stabilizing agents specified above in the table respectively added n lieu of polyethylene glycol 6000 (used as the low-melting fat- or oil-like substance in accordance with the invention) each in the same amount as the latter. The test results clearly indicate that the composition according to the invention is superior in the stability of ATP-2Na to the controls.

EXAMPLE 2

The same formulation as used in Example 1 was used except that ethanol was used in lieu of water. A solution of polyethylene glycol 6000 (used as the low-melting fat- or oil-like substance) in ethanol was added to ATP-2Na and other ingredients, and the mixture was kneaded and granulated using an agitator-granulator (Fuji Sangyo model VG 10 vertical granulator). The granulated composition was dried, sieved, supplemented with magnesium stearate, and tableted on a tableting machine using a 4.5 R punch (6.0 mm φ) at a pressure of 1.0 ton/cm². The thus-obtained tablets, each weighing 90 mg, were coated with the enteric coating composition (solids 10 mg/tablet) specified below, in which the major component was Eudragit L30D-55, using Accela Coater 24 (Manesty, Great Britain). The enteric coated tablets were further coated with the sugar coating composition specified below in which granulated sugar, talc, pullulan and so forth were used, on a coating pan (12 inches) to give sugar-coated tablets each weighing 200 mg.

The final tablets were tested for storage stability in the same manner as in Example 1. The results obtained are shown below.

| Material | Per tablet |
|---|---|
| Enteric coating | |
| Plain tablet | 90.0 mg |
| Eugragit L30D-55 | 23.0 (6.9 as solids) |
| Tween 80 | 0.7 |
| Polyethylene glycol 6000 | 0.3 |
| Talc | 2.1 |
| (Water) | (23.0 μl) |
| Total | 100.0 mg |
| Sugar coating | |
| Enteric coated tablet | 100.0 mg |
| Titanium oxide | 1.0 |
| Pullulan PI-20 | 0.8 |
| Avicel PH101 | 0.8 |
| Talc | 52.8 |
| Granulated sugar | 44.6 |
| (Water) | (20 μl) |
| Total | 200.0 mg |

| Results of storage stability testing | | |
|---|---|---|
| Item | Invention A | Control B |
| Initial | (100) | (100) |
| After storage at 60° C. for 1 week | 94 | 69 |
| After storage at 40° C. for 4 weeks | 99 | 90 |

The above results show that ATP-2Na is very stable in the composition according to the invention as compared with the control.

EXAMPLE 3

Tablets were prepared by the procedure of Example 1 according to the formulation given below using various low-melting fat- or oil-like substances in varied amounts as specified below. The tablets were then subjected to enteric coating and sugar coating by the procedure of Example 2. The sugar-coated tablets thus obtained were tested for storage stability in the same manner as in Example 1. The results are shown below.

| | Invention | | | | Control |
|---|---|---|---|---|---|
| | A | B | C | D | E |
| Formulation Material | | | | | |
| ATP-2Na | 20.0 mg | 20.0 mg | 20.0 mg | 20.0 mg | 20.0 mg |
| Lactose | 51.1 | 46.7 | 49.5 | 49.5 | 55.5 |
| Corn starch | 10.0 | 10.0 | 10.0 | 10.0 | 10.0 |
| Stearyl alcohol | 4.4 | 8.8 | — | — | — |
| Sorbitan fatty acid ester | — | — | 6.0 | — | — |
| Sucrose fatty acid ester | — | — | — | 6.0 | — |
| Hydroxypropylcellulose L | 2.5 | 2.5 | 2.5 | 2.5 | 2.5 |
| (Ethanol) | (50 μl) | (50 μl) | (50 μl) | (50 μl) | (50 μl) |
| Subtotal | 88.0 mg | 88.0 mg | 88.0 mg | 88.0 mg | 88.0 mg |
| Corn starch | 1.5 | 1.5 | 1.5 | 1.5 | 1.5 |
| Magnesium stearate | 0.5 | 0.5 | 0.5 | 0.5 | 0.5 |
| Total | 90.0 mg | 90.0 mg | 90.0 mg | 90.0 mg | 90.0 mg |
| Results of storage stability testing Item | | | | | |
| Initial | (100) | (100) | (100) | (100) | (100) |
| After storage at 60° C. for 1 week | 95 | 97 | 90 | 92 | 69 |

| | Invention | | | | Control |
|---|---|---|---|---|---|
| | A | B | C | D | E |
| After storage at 40° C. for 4 weeks | 99 | 100 | 98 | 98 | 90 |

The above test results show that the compositions according to the invention which contain a low-melting fat- or oil-like substance have good storage stability as far as the content of ATP-2Na is concerned.

What is claimed is:

1. A stabilized pharmaceutical composition which comprises a pharmaceutically effective amount of disodium adenosine triphosphate and an amount effective to stabilize disodium adenosine triphosphate against decomposition of a low-melting fat- or oil-like substance having a melting point of about 20° to 90° C.

2. The stabilized pharmaceutical composition according to claim 1, wherein the composition is in the form of tablets.

3. The stabilized pharmaceutical composition according to claim 1 or 2, wherein the low-melting fat or oil-like substance is hydrocarbons, higher fatty acids, higher alcohols, polyhydric alcohol fatty acid esters, polyhydric alcohol higher alcohol esters and alkylene oxide polymers or copolymers, any of which having a melting point of about 20° to 90° C.

4. The stabilized pharmaceutical composition according to claim 1 or 2, wherein when the low-melting fat or oil-like substance is added in the solid form, its amount being in the range of about 0.1 to 3 parts by weight per part by weight of disodium adenosine triphosphate.

5. The stabilized pharmaceutical composition according to claim 1 or 2, wherein when the low-melting fat or oil-like substance is added in the liquid form, its amount being in the range of about 0.1 to 3 parts by weight per part by weight of disodium adenosine triphosphate.

6. A method for stabilizing of a pharmaceutical composition containing a pharmaceutically effective amount of disodium adenosine triphosphate against decomposition of the disodium adenosine triphosphate which comprises incorporating into said composition an amount effective to stabilize the disodium adenosine triphosphate of a low-melting fat- or oil-like substance having a melting point of about 20° to 90° C. and molding the resulting mixture under pressure.

7. The method according to claim 6, wherein the incorporation is effected by blending, kneading, comalaxating, sieving or agitating.

* * * * *